US009290790B2

(12) United States Patent
Azevedo Pina Vaz et al.

(10) Patent No.: US 9,290,790 B2
(45) Date of Patent: Mar. 22, 2016

(54) FLUORESCENT METHOD OF DETECTING MICROORGANISMS RESISTANT TO A THERAPEUTIC AGENT

(75) Inventors: Cidália Irene Azevedo Pina Vaz, Oporto (PT); Acácio Agostinho Goncalves Rodrigues, Oporto (PT); Isabel Cristina Santos Silva De Faria Ramos Antunes, Oporto (PT); Ana Sofia Quinta E Costa De Oliveira Morais, Oporto (PT); Ana Teresa Pinto E Silva, Oporto (PT); Ana Isabel Silva Dias, Oporto (PT); Rita Daniela Teixeira Dos Santos, Setúbal (PT)

(73) Assignee: UNIVERSIDADE DO PORTO, Oporto (PT)

( * ) Notice: Subject to any disclaimer, the term of this patent is extended or adjusted under 35 U.S.C. 154(b) by 0 days.

(21) Appl. No.: 14/123,757

(22) PCT Filed: Jun. 4, 2012

(86) PCT No.: PCT/IB2012/052807
§ 371 (c)(1),
(2), (4) Date: Mar. 20, 2014

(87) PCT Pub. No.: WO2012/164547
PCT Pub. Date: Dec. 6, 2012

(65) Prior Publication Data
US 2014/0199703 A1    Jul. 17, 2014

(30) Foreign Application Priority Data

Jun. 3, 2011   (PT) ........................ 105744

(51) Int. Cl.
*C12Q 1/04*    (2006.01)
*C12Q 1/18*    (2006.01)
(52) U.S. Cl.
CPC ... *C12Q 1/18* (2013.01); *C12Q 1/04* (2013.01)
(58) Field of Classification Search
IPC .............................................. C12Q 1/18,1/04
See application file for complete search history.

(56) References Cited

U.S. PATENT DOCUMENTS 8,609,364 B2 * 12/2013 Walsh et al. .................. 435/32
2009/0068696 A1 * 3/2009 Frimodt-Moller ..... C12Q 1/045
435/19

FOREIGN PATENT DOCUMENTS

EP        0 118 274 A1    9/1984
WO    WO 2009/095258 A1    8/2009

OTHER PUBLICATIONS

Singh M. Rapid Test for Distinguishing Membrane Active Antibacterial Agents. J of Microbiological Methods 67(1)125-130, Oct. 2006.*
Pina-Vaz et al. (2005). Safe susceptibility testing of *Mycobacterium tuberculosis* by flow cytometry with the fluorescent nucleic acid stain SYTO 16. *Journal of Medical Microbiology*, 54(1), 77-81.
Pina-Vaz et al. (2001). Cytometric approach for a rapid evaluation of susceptibility of *Candida* strains to antifungals. *Clinical Microbiology and Infection*, 7(11), 609-618.
Pina-Vaz et al. (2004). Novel Method Using a Laser Scanning Cytometer for Detection of *Mycobacteria* in Clinical Samples. *Journal of Clinical Microbiology*, 42(2), 906-908.
Notification of Transmittal of the International Search Report and the Written Opinion of the International Searching Authority, or the Declaration, including an International Search Report and Written Opinion of the International Searching Authority, mailed Oct. 25, 2012 in connection with PCT International Application No. PCT/IB2012/052807, filed Jun. 4, 2012.

* cited by examiner

*Primary Examiner* — Ralph Gitomer
(74) *Attorney, Agent, or Firm* — John P. White; Cooper & Dunham LLP (57) ABSTRACT

This invention relates to an antimicrobial susceptibility test made upon pure microbial cultures—a laboratory culture containing a single species of organism—or directly from biological samples uncultured. Some preferred embodiments do not require the use a pure culture obtained from a biological product which would otherwise take at least 24 hours for the microorganisms to grow—so, is performed an antimicrobial susceptibility test directly from uncultured biological samples like urine, blood cultures or water by fluorescence analysis.

19 Claims, 7 Drawing Sheets

FLUORESCENT METHOD OF DETECTING MICROORGANISMS RESISTANT TO A THERAPEUTIC AGENT

CROSS-REFERENCE TO RELATED APPLICATIONS

This application is a §371 national stage of PCT International Application No. PCT/IB2012/052807, filed Jun. 4, 2012, claiming priority of Portuguese Patent Application No. 105744, filed Jun. 3, 2011, the contents of each of which are hereby incorporated by reference in their entirety.

TECHNICAL FIELD OF THE INVENTION

The present invention relates to a kit and a method of detecting the resistant microorganisms to a therapeutic agent and the determination of the underlying resistance mechanisms.

BACKGROUND OF THE INVENTION

Nowadays, there is a major need to abbreviate and improve current laboratory procedures for the detection and most of all susceptibility evaluation of microorganisms. An ideal diagnostic technology would give susceptibility profile timely in order to allow the institution of appropriate therapy based on it.

In the case of the most serious infections associated namely to septic shock, speed is of the essence. It has been shown that the risk of mortality would increase substantially by the hour if appropriate antimicrobial therapy is delayed.

The current gold-standard diagnostic methods are based on culture which is slow, labour intensive, providing phenotypic identification and antimicrobial susceptibility testing, requiring 48-72 h after collection of the samples. Empiric therapy has to be initiated often with a large spectrum antibiotic, leading to the increase of antimicrobial resistance.

Using classic tests, biological products like urine have to be cultivated in solid media and only then identification and susceptibility evaluation could take place. Blood are usually inoculated on broth media (blood cultures) and analysed automatically; when become positive they are plated on solid media and only after 24 h at least, colonies are formed for the susceptibility evaluation. On the other hand another 24 h are necessary for susceptibility profile determination as they are based on the ability to grow in the presence of a panel of drugs.

Clinical resistance could be related to lack of antimicrobial susceptibility of the strain but also to low levels of active antimicrobial drug on infection local. Biochemical protocols are available for only few drugs e.g. vancomycin, gentamicin or amikacin and they could be inactive.

SUMMARY OF THE INVENTION

This invention relates to an antimicrobial susceptibility test made upon pure microbial cultures—a laboratory culture containing a single species of organism or directly from biological samples—uncultured—by flow cytometry. Some preferred embodiments is to take do not required the use a pure culture obtained from a biological product—which takes at least 24 hours for the microorganisms to grow—so, is performed an antimicrobial susceptibility test directly from biological samples—uncultured like urine, blood cultures or water by fluorescence analysis as a flow Cytometry.

The disclosed subject matter relates to a method for detecting resistant microorganisms to a therapeutic agent in a biological sample, comprising the following steps:
  a. inoculate the said sample, on a first tube with, and on a second tube without, at least one therapeutic agent and incubated it;
  b. add to both tubes a fluorescent marker;
  c. perform a fluorescence analysis for obtaining one or more fluorescence or growth parameters for each of the two tubes;

wherein the microorganisms resistant phenotype of the biological sample to said therapeutic agent is obtained by comparing the one or more fluorescence parameters between the two tubes.

The disclosed subject matter also relates to a method for detecting resistant microorganisms (a bacteria, a fungi or a protists) to a therapeutic agent in a biological sample. Namely directly from biological samples—unculture—like a sample of urine, blood culture, water or a suspension of microorganisms obtained from pure cultures, comprising the following steps:
  a. inoculate the said sample, uncultured, on a first tube with, and on a second tube without, at least one therapeutic agent; preferentially further including at least one lysing agent and/or a buffer, and/or a suitable culture medium, or put the sample on a separation serum tube; and incubated it;
  b. add to both tubes a fluorescent marker;
  c. perform a flow cytometric analysis for obtaining one or more flow cytometric parameters for each of the two tubes;

wherein the microorganisms resistant phenotype of the biological sample to said therapeutic agent is obtained by comparing the one or more flow cytometric parameters between the two tubes.

In other embodiment the one or more flow cytometric parameters comprise forward scatter and/or side scatter and/or fluorescence parameters. The parameters of the fluorescence scatter signal could be intensity, spectral profile and/or cell count.

In other embodiment of the present invention, the method disclosed further comprises one or more of the preparatory steps:
  identify the type of microorganism present in the biological sample and, accordingly, select the therapeutic agent or agents, namely if the type is gram-positive or gram-negative;
  concentrate the biological sample and remove, if present, any detritus, for example detritus from blood samples, urine or other biological product; preferentially by centrifugation, filtration or use a separation serum tube and centrifugate.

In another embodiment of the present invention, the incubation time of the sample may vary between 30 min-2 h, preferably between 30-60 min.

In another embodiment of the present invention, the incubation temperature of the sample is between 30-40° C., preferably between 25-35° C.

In another embodiment of the present invention, the reaction time of the step b) with the fluorescent marker may be between 5-60 minutes.

In other embodiment of the present invention, for the determination of microorganisms resistance mechanisms the biological sample in step c) may further comprise an enzymatic inhibitor, for example, in the case of detection of Extended Spectrum Beta-Lactamases (ESBLs) presence. The preferred enzymatic inhibitor could be clavulanic acid or tazobactam, or their mixtures, among others.

In another preferred aspect of the present invention, the method further comprise the following step in order to detect of microorganisms resistance mechanisms, as for example due to the presence of carbapenemases—enzymes that degradate carbapenems, an important mechanism of resistance (the Hodge test is recommended taking another 24 hours, being cumbersome and difficult to interpret):

i. inoculate the said sample with a carbapenem and incubated it;
ii. remove the microorganism of the biological sample, preferably by filtration;
iii. add a strain with known behaviour—i.e., a control strain with a known dose-effect curve, as for example incubating a serial concentration of a carbapenem with an microorganism as *Escherichia coli*, ATCC strain 25922 by flow cytometry;
iv. add to both samples a fluorescent marker;
v. perform a flow cytometric analysis for obtaining one or more flow cytometric parameters for each of the two tubes;
vi. comparing the profile generated with the control strain, In the presence of carbapenemases the tested strain will degradate the carbapenem so the active drug is reduced; the effect of carbapenems on the type strain is reduced. If the effect of a certain concentration of carbapenem is inferior to expected, the microorganism is a carbapenemase producer.

In a more preferred embodiment, of the present invention, the method further comprise the following step in order to detect of microorganisms resistance mechanisms, as for example due to the presence of carbapenemases:

obtain a flow cytometric dose-effect curve, incubating a serial concentration of a carbapenem with a microorganism as *Escherichia coli*, ATCC strain 25922 by flow cytometry;
facing a resistant strain to carbapenems, remove the microorganism by filtration from the test tube containing the strain after incubation with a certain concentration of the carbapenem;
this filtrate is now incubated with the type strain (ATCC) and its effect analysed by flow cytometry; its effect is compared with the expected result regarding the dose-effect curve.

In another preferably embodiment, the therapeutic amount of any drug in a biological fluid could further be evaluated based on the same methodology.

In a most preferably embodiment of method for detecting resistant microorganisms to a therapeutic agent in a biological sample, the said microorganism is a *Staphylococcus* spp, *Streptococcus* spp, *Enterococcus* spp; Enterobacteriacea like *Escherichia coli*, *Klebsiella pneumonia*, *Proteus* spp; non-fermentative bacteria like *Pseudomonas aeruginosa*, *Acinetobacter baummanii* or *Burkloderia cepaciae*; *Neisseria* spp, *Haemophilus* spp; *Mycobacterium* spp and *Nocardia* spp; *Legionella* spp and anaerobic bacteria; fungi like *Candida* spp, *Cryptococcus neoformans*, *Pneumocystis jirovecii* and moulds like *Aspergillus* spp; parasites like *Giardia* spp, or other similar microorganism.

In another preferably embodiment of method for detecting resistant microorganisms to a therapeutic agent in a biological sample, the therapeutic agent could be an antbacterial drug like penicillins, cephalosporins, other beta-lactams (carbepenems, aztreonam) macrolides, quinolones, aminoglycosides, glycopeptides, a lipopeptide, tetracyclines and others (e.g. colistin, chloramphenicol, clindamycin, fosfomycin, linezolid, nitrofurantoin, sulphonamide, rifampin, trimethoprim, trimethoprim-sulfamethoxazole or tigecycline); an antifungal like polyenes, 5-fluorocytosine, azoles or echinocandins or other similar therapeutic agent.

In other preferably embodiment of method for detecting resistant microorganisms to a therapeutic agent in a biological sample, the fluorescent marker may be a nucleic acid stain, a metabolic stain, a membrane potential stain, a probe for organelles, fluorescent tracer of cell morphology and fluid flow, probe for cell viability, proliferation and function or probe for reactive oxygen species. Most preferably, the fluorescent marker is acridine dye, cyanine dye, fluorone dye, oxazin dye, phenanthridine dye, or a rhodamine dye.

In a different embodiment, the antifungal susceptibility to moulds may additionally be performed inoculating spores on Bactec Mycosis IC/F vials or MGIT tubes with and without antifungals like: amphotericin B, voriconazole and fluconazole; time to became positive—fluorescence emission—will be recorded by Bactec equipment. On susceptible strains vials with antifungal will take at least twice the time to become positive compared to control vial—without antifungal.

It is still the subject of the present invention a kit for detecting the resistant microorganisms to a therapeutic agent that comprises the method described above.

In one more embodiment of the present invention, the kit may additionally present the following solutions: a therapeutic agent and/or a fluorescent marker.

In yet another embodiment of the present invention, the kit may additionally comprise the following solutions: a buffer, a lysing agent and/or culture medium, and/or an enzymatic inhibitor and/or a control strain.

It is still the subject of the present invention fluorescence device for carrying out the methods of any one of the previous claims. The fluorescence could be a flow cytometer or a BACTEC MGIT—*Mycobacteria* Growth Indicator Tube.

The disclosed subject matter allows the evaluation the susceptibility of a microorganism—namely infectious agents—to the main antimicrobial agents either from colonies or from the biological samples; moulds have a different protocol. The disclosed subject matter further allows the detection of the mechanisms of resistance and even microbiological assay quantification of the drug in different biological samples.

GENERAL DESCRIPTION OF THE INVENTION

The laboratory methods for susceptibility profile used in routine clinical laboratory requires a minimum time of 48 hours. This delay is due to the fact that known methods are based on the growth of microorganisms. Rather, the antimicrobial susceptibility evaluation by fluorescence analysis, namely flow cytometry based on the evaluation of the physiological state of the cell after exposure to the drug for a short period of time. The determination of morphological lesions or physiological activity is not possible by classical methodology.

Many developments have emerged in the field of microbiology, particularly as regards the identification of microorganisms using molecular biology techniques. However, this technology presents a limitation as it can only be applied to organisms whose genome is known. Another drawback relates to its high cost. In addition, molecular biology only very occasionally provides information on the susceptibility of the microorganism as, only occasionally, the presence of a specific gene is known to confer resistance to a particular drug. This direct relationship is established on the specific case of rifampicin regarding resistance of *Mycobacterium tuberculosis* and resistance to methicillin on *Staphylococcus aureus*.

The characteristics that allow the test to be performed directly from the product are:
- the fact that these products have a sufficient cell density (preferably exceeding $10^5$) for flow cytometry screening
  - The blood culture is submitted to a prior incubation providing, afterwards when positive, the microorganism are at the required cellular density to perform susceptibility tests;
  - Urinary samples, the criteria for infection corresponds to a cell density exceeding $10^5$ cells per milliliter.
- in both products, microorganisms are found in exponential phase—this is required because the susceptibility evaluation of some types of antimicrobial drugs need to have microorganisms in the exponential phase due to their mode of action.

The innovative application of flow cytometry is the possibility of performing a multiparametric evaluation of a cell population of microorganisms dynamically, over time, and to correlate this with the study of its replicative capacity. To demonstrate a rapidly lethal activity of a drug by the conventional method we have to prove that the cell is unable to replicate. By flow cytometry, we could be able to demonstrate after a few minutes incubation time with a specific drug, a serious injury of cell membrane, meaning death. Moreover, mechanisms of action and even more importantly resistance mechanisms could be investigated by Flow Cytometry. Additionally, this new approach allows the study of drug combinations often use on critical patients without previous in vitro evidence of synergic effect.

DESCRIPTION OF THE FIGURES

The following figures provide preferred embodiments for illustrating the description and should not be seen as limiting the scope of invention.

DETAILED DESCRIPTION OF THE INVENTION

Figure 1:
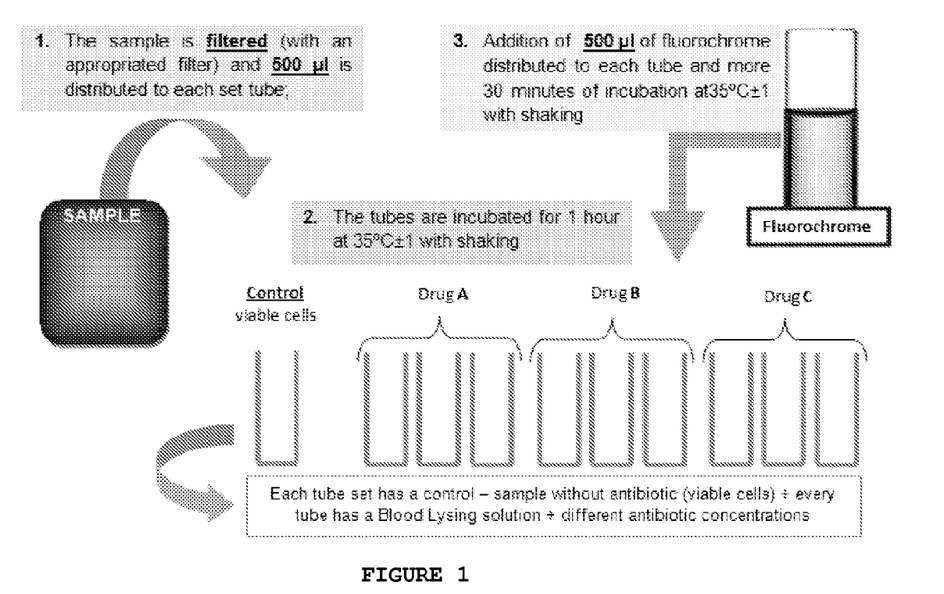
FIG. 1: Scheme of the methodology for a rapid antimicrobial susceptibility evaluation directly from positive blood cultures or urine samples before flow cytometry acquision.
Figure 2:
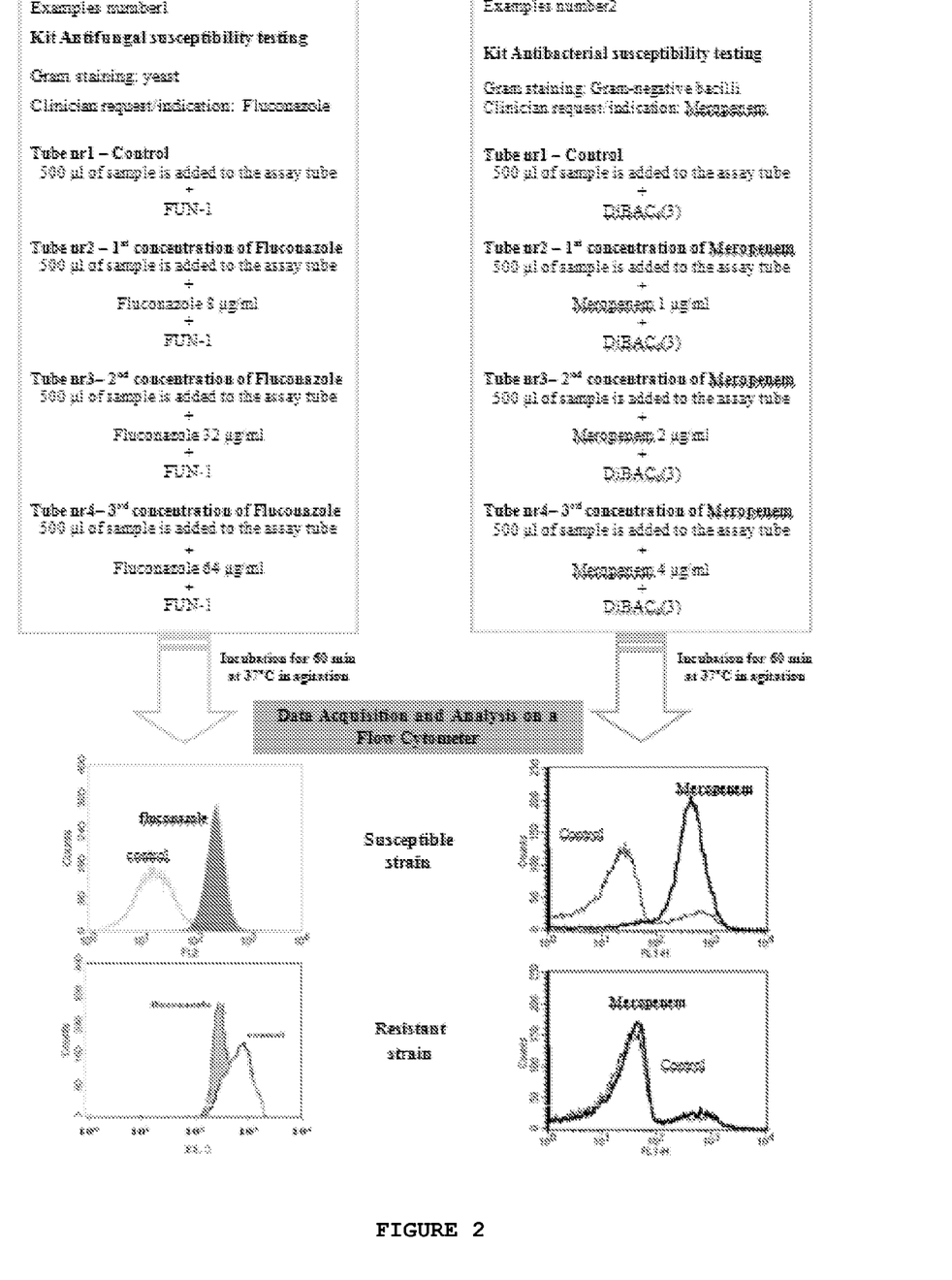
FIG. 2: Scheme of two distinct embodiments of the present invention—the method of detecting the susceptibility of a microorganism to a therapeutic agent using positive blood cultures or urine samples implemented and the results obtained with typical susceptible and resistant strains.
Figure 3:
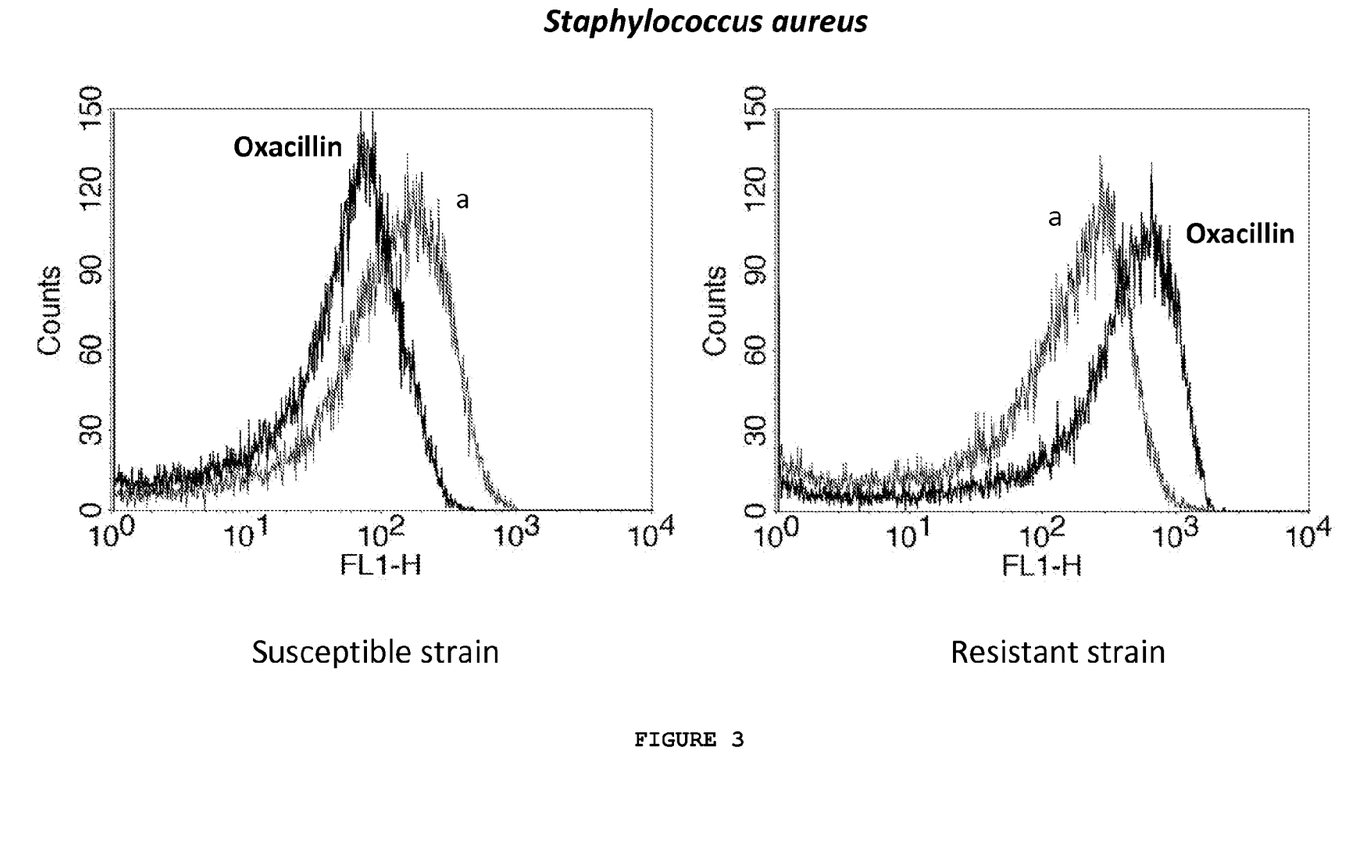
FIG. 3: Flow cytometry histograms of a typical example of a susceptible (MSSA) and resistant *Staphylococcus aureus* to oxacillin (MRSA) after 2 hours incubation time and staining with FDA.
Figure 4:
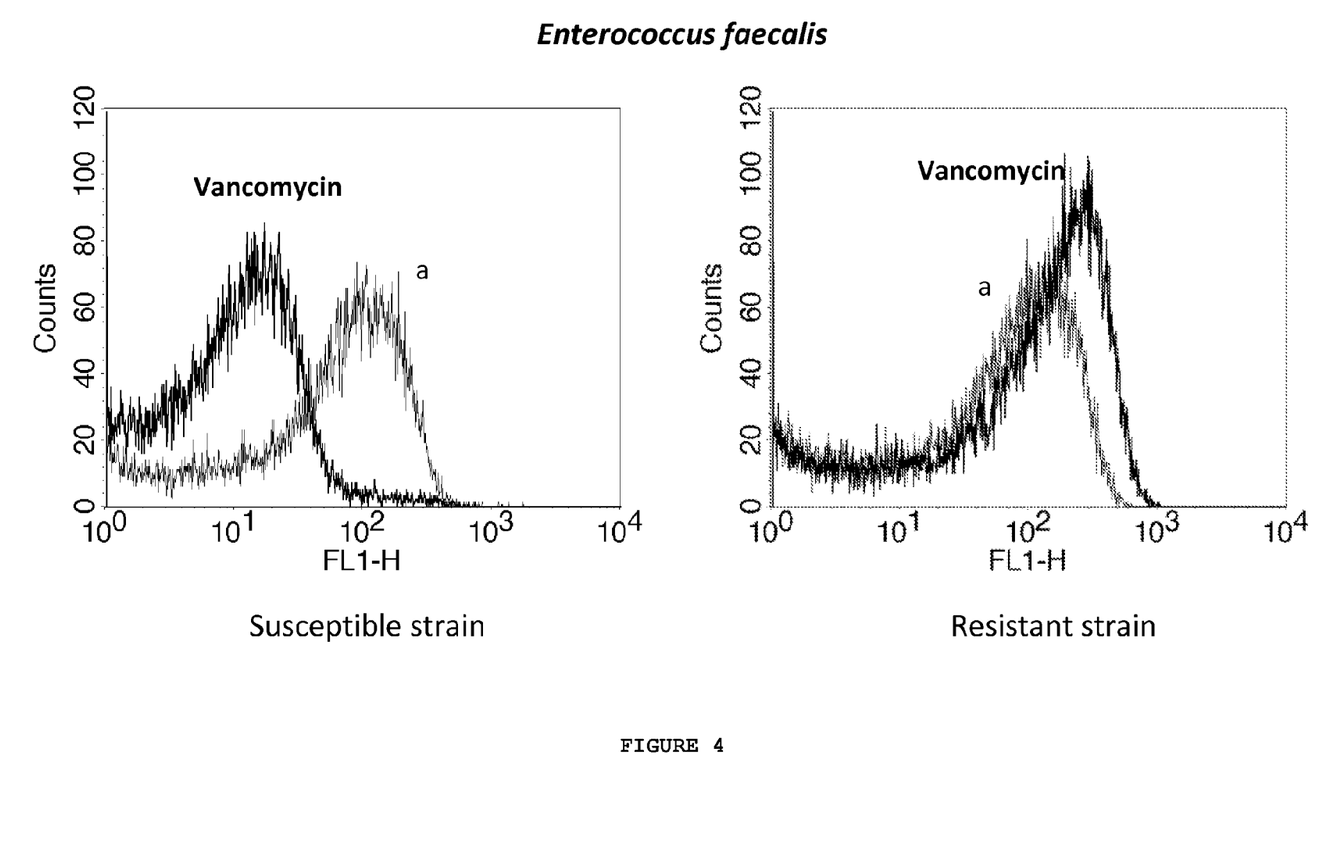
FIG. 4: Flow cytometry histograms of a typical example of a susceptible and resistant *Enterococcus faecalis* to vancomycin after 1 hour incubation time and staining with FDA.
Figure 5:
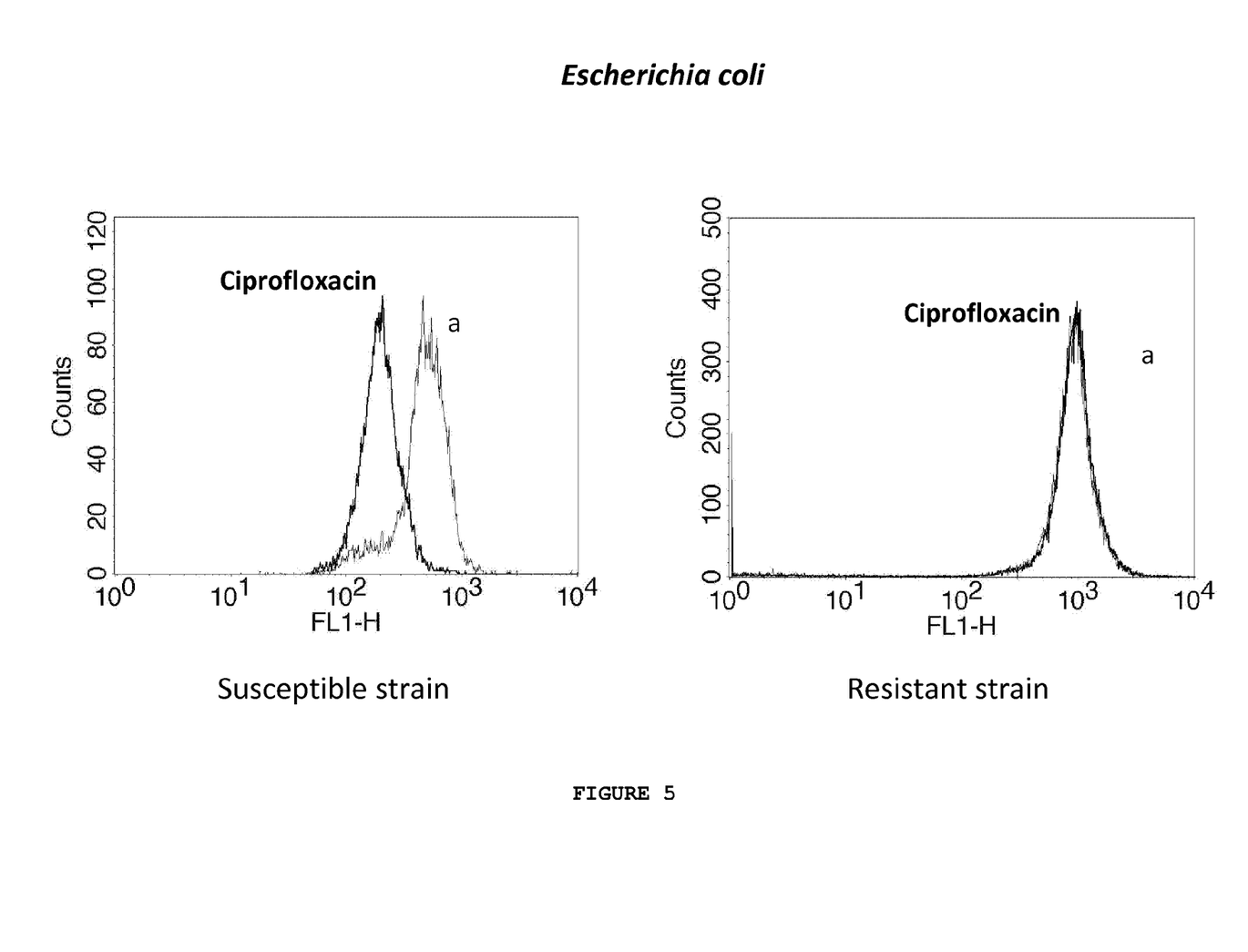
FIG. 5: Flow cytometry histograms of a typical example of a susceptible and resistant *Escherichia coli* to quinolones, namely ciprofloxacin after one hour incubation time and staining with SYBR Green.
Figure 6:
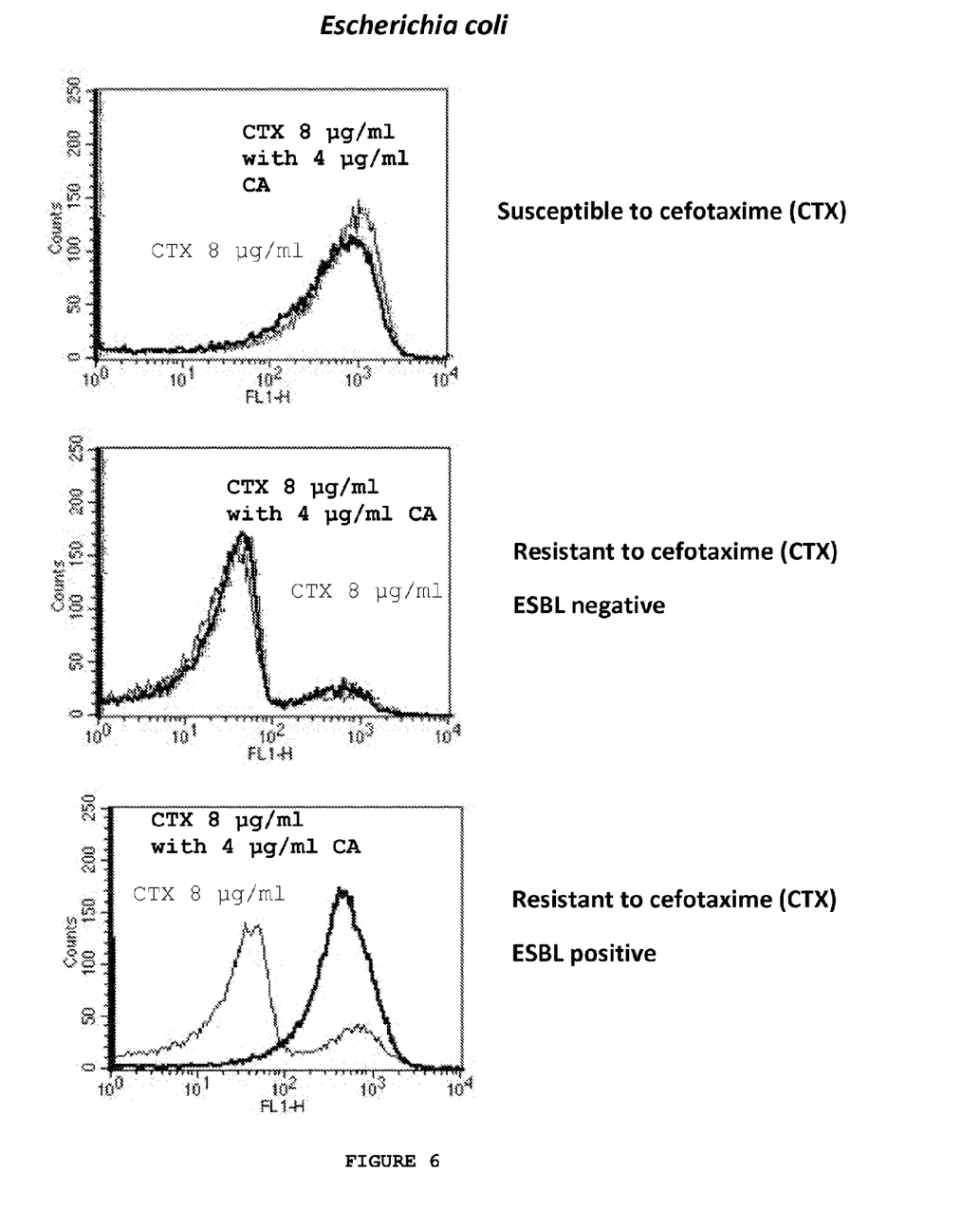
FIG. 6: Flow cytometry histograms of a typical example of *Escherichia coli* susceptible and resistant to cefotaxime (CTX) after incubation during one hour with the drug and stained with DiBAC$_4$(3); in case of resistant to CTX incubate with CTX with and without clavulanic acid (CLA) and stained with DiBAC$_4$(3). ESBL positive strain behaves as susceptible when incubated with CLA.
Figure 7:
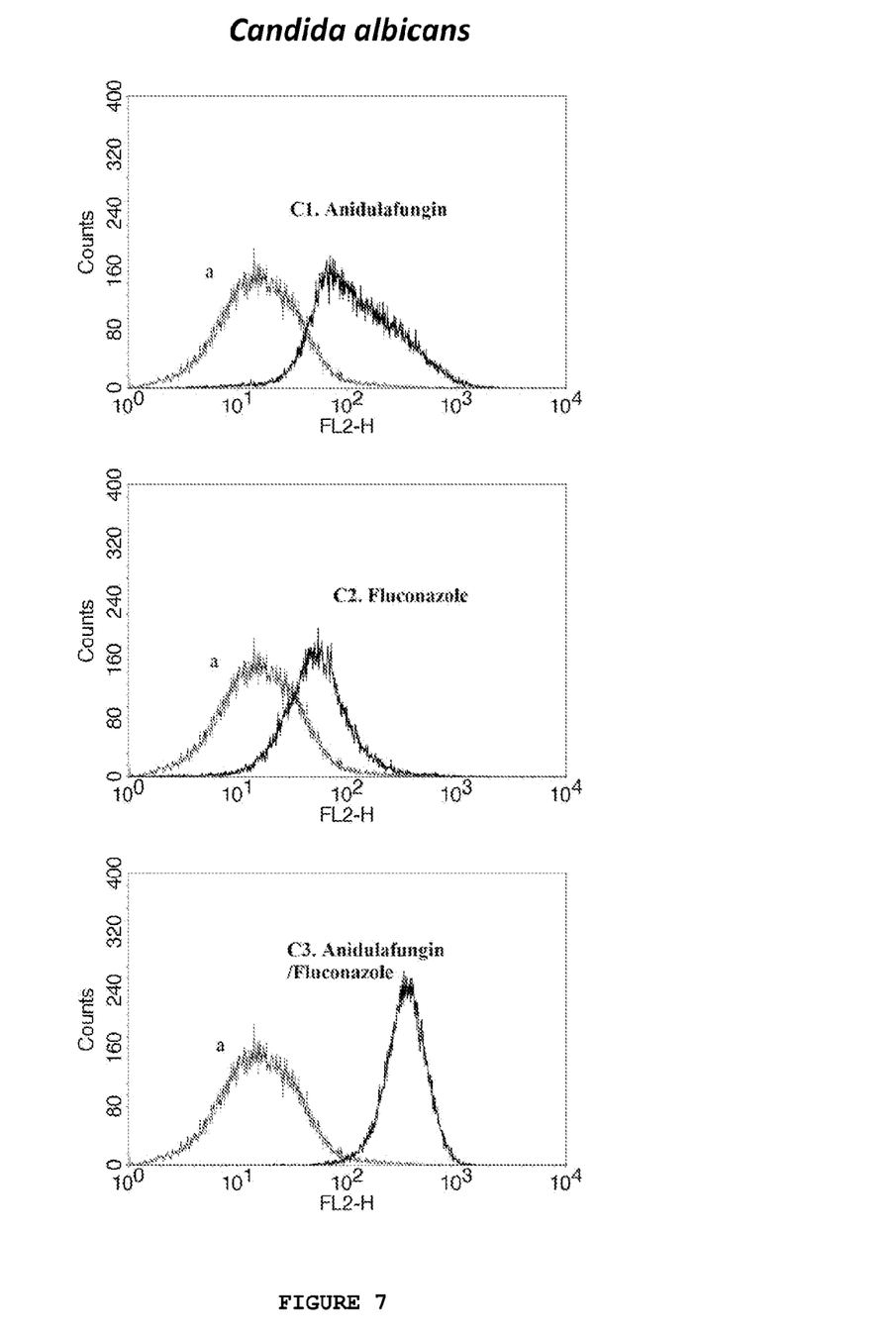
FIG. 7: Flow Cytometry histograms of typical example of *Candida albicans* strain after incubation one hour with anidulafungin, fluconazole or the associations of both and stained with DiBAC4(3). a. control cells (without antifungals) and C after incubation with the drugs (C1-anidulagungin, C2-fluconazole and C3-anidulafungin and fluconazole)

Classic susceptibility methods are based on pure cultures in solid media. Suspensions of microorganisms are prepared and according to it adequate susceptibility cards/panels (example: Gram-negative bacilli; gram-positive cocci; fungi, etc) regarding automatic methods (VITEK 1 or VITEK 2 System—BioMerieux; BD Phoenix System—Becton-Dickinson Biosciences; MicroScan WalkAway System—Dade Behring).

Other manual tests are available like broth macrodilution and microdilution tests, E-test (AB BIODISK), Disc diffusion test and dry-form panels (TREK Diagnostics).

All of them are based on the study microorganism's capacity to replicate in the presence of different antimicrobials.

Firstly the biggest disadvantage is that they are performed from colonies in solid media which needs at least 24 h to grow. Despite there are available semi-automated methods they are based on growth detection which take time to give results (min. 18-24 h), they need highly experienced personnel and are expensive.

BioMolecular Methods (not Implemented in all Routine Laboratory).

Molecular methods represented a revolution for microbiology diagnostic laboratory test mostly related with the microorganisms identification and only rarely it can help in susceptibility evaluation (Multiplex PCR, Microarrays, etc).

In fact there are several genes involved in resistance mechanisms, leading many times to sequencing steps. Normally there is a lack of correlation between genotype and phenotype. Despite being highly sensitive and specific—do not give any information regarding viability and are expensive.

1. Preparation of a Microbial Suspension
1.1 Blood Cultures or Urine Sample

From a positive blood culture or urine sample:
- Perform a Gram staining (maximum: 10 minutes) or mass spectrometry analysis (Maldi-TOF) in order to guide the consequent analysis. This previous step will provides us essential information about the microorganism, namely in terms of:
  - Bacteria: cocci or bacilli; Gram-positive or Gram-negative—leading to the choice of antibiotics to be tested;
  - Fungi
- Filter (in order to take off haematological cells and big debris) and transfer the blood culture or urine to a vial containing a blood lysing solution (aqueous solution of $NH_4Cl$, $KHCO_3$ and EDTA) or
- Transfer to a separator serum tube (e.g. vacoutainer gel tube) and centrifuge. Blood cells will stay in the bottom of the gel, microorganisms on the top of the gel
- Make a microbial suspension on sterile, filtered culture medium.

1.2 From Pure Cultures

Make a microbial suspension from a colony in sterile and filtered broth culture medium (for example: Mueller-Hinton) and incubate until exponential growth phase.

1. Incubate the bacterial suspension at 37° C. and 150 strokes per minute, until bacteria reach the early exponential growth phase (preferably when optical density of 0.2 at 600 nm wavelength) in sterile and filtered (0.22 μm) Mueller-Hinton broth (Difco™)
2. Dilute the broth culture to an O.D.=0.06 (aprox. $10^6$ cells per ml, which is the optimal cellular density to read in a flow cytometer) or alternatively adjusted to 0.5 MacFarland and afterwards diluted preferably 1:100 in broth culture.

2. In Vitro Antimicrobial Treatment

Obtain the cellular density for susceptibility test by flow cytometry, could b e.g. $10^6$ cells/ml.

Transfer the microbial suspension to a set of vials with different antimicrobial drugs (at breakpoint concentrations) including a control vial (without antimicrobial drug);

Incubate the vials according to the antimicrobial drug (0.5-2 hours);

Add appropriated fluorochrome (depending on the antimicrobial drug) according to previous optimized protocol.

3. Flow Cytometric Analysis

Acquisition settings are defined using microsphere samples by adjusting voltage to the third logarithmic (log) decade of all fluorescence channels. FSC threshold is used. Samples are analyzed in the FL1, FL2 and FL3 fluorescence channel depending on the fluorescent probe, using two dot plots: SSC versus FSC and SSC versus Fluorescence. Numerical results are expressed using intensity of fluorescence and/or percentage of stained cells.

The equipment is a flow cytometer (for example a FACS-Calibur BD Biosciences, Sydney, Australia) with three PMTs equipped with standard filters (FL1: BP 530/30 nm; FL2: BP 585/42 nm; FL3: LP 670 nm), a 15 mW 488 nm Argon Laser and operating with cell Quest Pro software (version 4.0.2, BDBiosciences, Sydney). The Flow Cytometry data file format used was FCS $2.0^a$.

EXAMPLES

The following examples provide preferred embodiments and should not be seen as limiting the scope of invention.

Example No. 1

*Escherichia coli* Susceptibility Evaluation to Quinolones

Microbial agent: *Escherichia coli*
Drug tested: Quinolone—ciprofloxacin
[2 breakpoint concentrations: 1 and 4 µg/ml]
Fluorochrome used: SYBR Green, a membrane permeant dye that binds to double stranded DNA structure.

1. Distribute the bacteria suspension with the concentration of $10^6$ cells per ml to serial of vials containing:
   Ciprofloxacin at 1 µg/ml;
   Ciprofloxacin at 4 µg/ml;
   Viable control (without ciprofloxacin).
2. After thirty minutes of incubation at 35° C. and 150 strokes per minute, centrifuge the set of vials at 10000 rpm during five minutes.
3. Add SYBR Green (prepared in TE, pH=7.5) at a final dilution of 1:100000 for 30 minutes in the dark.
4. Perform Flow Cytometric acquisition at 530/30 nm—FL1;
   compare the intensity of fluorescence of treated cells with non-treated cells.

Results Interpretation Criteria:

Ciprofloxacin acts by inhibiting DNA gyrase and blocks DNA replication leading to less double stranded DNA which is the target to the fluorochrome SYBR Green. Therefore, it is expected that Susceptible strains (MIC values<1 µg/ml) to Ciprofloxacin show a reduction of double stranded DNA—corresponding to less intensity of fluorescence.

Calculate a staining index (SI) based on the ratio between intensity of green fluorescence (530/30 nm; FL-1) of treated cells and non-treated cells (viable control)
Susceptible bacteria if SI<1 with 1 µg/ml of ciprofloxacin;
Resistant bacteria if SI≥1 with 4 µg/ml of ciprofloxacin.

Example No. 2

Susceptibility Evaluation for Gram Negative Bacteria to Carbapenems

Microbial agent: *Pseudomonas aeruginosa*
Drug tested: Carbapenems—Meropenem
[3 breakpoint concentrations: preferably 1, 2 or 4 µg/ml]
Fluorochrome used: Bis-(1,3-dibutylbarbituric acid) trimethine oxonol (DiBAC$_4$(3)—a voltage sensitive lipophilic anion for the measurement of membrane potentials; depolarized cells show higher intensity of fluorescence while polarized cells show a lower value.

1. Distribute the bacteria suspension with the concentration of $10^6$ cells per ml to serial of vials containing:
   Meropenem at 1 µg/ml;
   Meropenem at 4 µg/ml;
   Viable control (without Meropenem)
2. After thirty minutes of incubation at 35° C. and 150 strokes per minute, add DiBAC$_4$(3) at a final concentration of 1 µg/ml for 30 minutes in the dark.
3. Perform Flow Cytometric acquisition at 530/30 nm—FL1; compare the intensity of fluorescence of treated cells with non-treated cells.

Results Interpretation Criteria:

Meropenem, is bactericide acting by inhibition the synthesis of the peptidoglycan layer of bacterial cell walls. Membrane depolarization can be rapidly detected by DiBAC$_4$(3) on susceptible strains. Depolarized cells show higher intensity of fluorescence while polarized cells show a lower value.

Calculate a staining index (SI) based on the ratio between intensity of green fluorescence (530/30 nm; FL-1) of depolarized cells following treatment with the antimicrobial and control cells (non-treated).
Susceptible bacteria SI<1 with 1 µg/ml of meropenem;
Resistant bacteria SI≥1 with 4 µg/ml of meropenem;

Example No. 3

*Staphylococcus aureus* Susceptibility Evaluation to Oxacillin

Microbial agent: *Staphylococcus aureus*
Drug tested: oxacillin
[2 concentration: 2, 4 µg/ml]
Fluorochrome used: FDA (fluorescein diacetate), a a fluorescent indicator of cell viability; viable cells upon hydrolysis by esterases, FDA forms fluorescein.

1. Distribute the bacteria suspension with the concentration of $10^6$ cells per ml to serial of vials containing:
   oxacillin at 2 µg/ml
   oxacillin at 4 µg/ml;
   Viable control (without oxacillin).
2. After 120 minutes of incubation at 35° C., add FDA 1 µg/ml and incubated for 60 minutes at the same conditions.
3. Perform Flow Cytometric acquisition at 530/30 nm—FL1; compare the intensity of fluorescence of treated cells with non-treated cells.

Results Interpretation Criteria:

Oxacillin is bactericide acting by inhibition the synthesis of the peptidoglycan layer of bacterial cell walls. Therefore, it is expected that Susceptible strains (MIC values≤2 µg/ml) to oxacillin show a reduction of metabolic activity—corresponding to less intensity of fluorescein fluorescence.

Calculate a staining index (SI) based on the ratio between intensity of green fluorescence (530/30 nm; FL-1) of treated cells and non-treated cells (viable control)
Susceptible bacteria SI<1 with 2 µg/ml of oxacillin;
Resistant bacteria SI≥1 with 4 µg/ml of oxacillin.

Example No. 4

Gram Positive Bacteria Susceptibility Evaluation to Vancomycin

Microbial agent: *Enterococcus faecalis*
Drug tested: Glicopepetide—vancomycin
[2 breakpoint concentrations: 4-16 µg/ml]
Fluorochrome used: FDA (fluorescein diacetate), a a fluorescent indicator of cell viability; viable cells upon hydrolysis by esterases, FDA forms fluorescein increasing fluorescence emission.
1. Distribute the bacteria suspension with the concentration of 10^6 cells per ml to serial of vials containing:
   vancomycin at 4 µg/ml
   vancomycin at 16 µg/ml;
   Viable control (without vancomycin).
2. After 60 minutes of incubation at 35° C. and 150 strokes per minute, add FDA 1 µg/ml and incubated for 30 minutes at the same conditions.
3. Perform Flow Cytometric acquisition at 530/30 nm—FL1; compare the intensity of fluorescence of treated cells with non-treated cells.

Results Interpretation Criteria:

Vancomycin is bactericide acting by inhibition the synthesis of the peptidoglycan layer of bacterial cell walls. Therefore, it is expected that Susceptible strains (MIC values<2 µg/ml) to vancomicyn show a reduction of metabolic activity—corresponding to less intensity of fluorescein fluorescence.

Calculate a staining index (SI) based on the ratio between intensity of green fluorescence (530/30 nm; FL-1) of treated cells and non-treated cells (viable control)
Susceptible bacteria SI<1 with 4 µg/ml of vancomycin;
Resistant bacteria SI≥1 with 16 µg/ml of vancomycin.

Example No. 5

Study of Resistance Mechanisms

Resistance by Extended-Spectrum β-Lactamases (ESBLs)
Microbial agent: *Klebsiella pneumoniae*
Drug tested: cefotaxime (CTX) and ceftazidime (CAZ)$_2$ breakpoint concentrations:
   −1 and 4 µg/ml for CTX
   −4 and 16 µg/ml for CAZ
Drug-inhibitor tested: clavulanic acid (CLA)-4 µg/ml
Fluorochrome used: Bis-(1,3-dibutylbarbituric acid) trimethine oxonol (DiBAC$_4$(3))—a voltage sensitive lipophilic anion for the measurement of membrane potentials.
1. Distribute the bacteria suspension with the concentration of 10$^6$ cells per ml to serial of vials containing:
   CTX at 1 µg/ml;
   CTX at 4 µg/ml;
   CTX at 1 µg/ml+4 µg/ml CLA;
   CTX at 4 µg/ml+4 µg/ml CLA;
   CAZ at 4 µg/ml;
   CAZ at 16 µg/ml;
   CAZ at 4 µg/ml+4 µg/ml CLA;
   CAZ at 16 µg/ml+4 µg/ml CLA
   Viable control (without cephalosporins)
2. After thirty minutes of incubation at 35° C. and 150 strokes per minute, add DiBAC$_4$(3) at a final concentration of 1 µg/ml for 30 minutes in the dark.
3. Perform Flow Cytometry analysis with appropriated protocol and read at 530/30 nm—FL1.

Results Interpretation Criteria:

ESBLs are detected based on their ability to hydrolyze cephalosporins (CTX and CAZ) but are inhibited by clavulanic acid (CLA), i.e., it is expected to detect a bacteria that are resistant to cephalosporins through the production of ESBLs when they become susceptible by the exposure to cephalosporins associated with CLA.

Calculate a staining index based on the ratio between intensity of green fluorescence (530/30 nm; FL-1) of depolarized cells (dead cells; cells with high intensity of fluorescence) following treatment with the highest concentrations of both cephalosporins (4 µg/ml of cefotaxime (CTX) and 16 µg/ml of ceftazidime (CAZ)) with and without the presence of CLA—in this specific case, denominated CLA Index.

CLA Index>1.5 (for at least one cephalosporin) ESBL producer bacteria
CLA Index≤1.5 ESBL negative producer bacteria Example No. 6

Susceptibility Evaluation of a Combination of Drugs from a Positive Blood Culture for Yeasts Filter and use the lysing agent or use a separator tube and centrifugate
Perform a Gram—yeasts or MaldiT of analysis—*Candida albicans*
Drug tested: anidulafungin and fluconazole isolated and in association
Fluorochrome used: FUN-1, a fluorescent marker used to study yeasts viability
NOTE: unviable cells show higher intensity of fluorescence than viable (non-treated cells)
After sixty minutes of incubation with the antifungal isolated and in association at 37° C., add FUN-1 at a final concentration of 0.5 µg/ml for 30 minutes in the dark.
Perform Flow Cytometric acquisition at 575 nm—FL2; an index of fluorescence is calculated as the sum of ratios between the fluorescence of treated cells with the association of antifungal and the fluorescence of cells treated with each individual antifungal. The association is categorized as synergic, indifferent or antagonistic.

Results Interpretation Criteria:

The evaluation of in vitro drug interaction are determined according to staining index (SI). The SI is calculated as the sum of mean intensity of fluorescence displayed by cells treated with drug combination (0.5×MIC of each drug) divided by the fluorescence of the drug alone. Hence, SI=(MIF AND+FLU/MIF AND)+(MIF AND+FLU/MIF FLU) (MIF-ration between mean intensity of fluorescence of treated cells and viable cells). An association is defined as "antagonism" for SI<1, "indifferent" for SI between 1-4 and "synergy" for a SI>4.

Example No. 7

Antifungal Susceptibility of *Aspergillus fumigatus*

Prepare a dense suspension of *Aspergillus fumigatus*;
Inoculate $10^7$ spores/ml in a serial of Bactec Mycosis IC/F vials or in MGIT tubes from automated Bactec equipments (Becton Dickinson);
Each serial include one vial or tube without antifungal (control), one with amphotericin B, one with posaconazole and one with voriconazole;
The vials or tubes are introduced in the respective Bactec equipment and the time to became positive recorded
Results Interpretation Criteria:
Susceptible strains incubated with antifungals would take more than the double time to became positive compared to control. MGIT tubes give quicker results than Bactec vials (ex. Control samples take 7±1 hour on Bactec vials versus 11±1 hour on MGIT tubes)

Example No. 8

Microbiological Antimicrobial Quantification from a Biological Fluid

Use a control strain with a known flow cytometric dose-effect curve when incubated with the antimicrobial we want to quantify;
Incubate the biological sample with the control strain
labelled the two previous samples with an adequate fluorescent marker to evaluate the antimicrobial effect;
obtain the flow cytometer fluorescence and scatter signals to generate a profile of said microorganism.
Results Interpretation Criteria:
Compare the flow cytometric profile generated with the control sample curve and infer the concentration present on sample.

The invention is of course not in any way restricted to the embodiments described and a person with ordinary skill in the art will foresee many possibilities to modifications thereof without departing from the basic idea of the invention as defined in the appended claims.

The following claims set out particular embodiments of the invention.

The invention claimed is:

1. A method for detecting, in an uncultured biological sample comprising microorganisms, the presence of a specific type of microorganism resistant to a predetermined therapeutic agent, comprising the following steps:
   a. making two microbial suspensions of the sample in culture media, one in a first tube with, and one in a second tube without, such predetermined therapeutic agent;
   b. incubating both such suspensions;
   c. adding to the tube containing each such suspension a fluorescent marker which is capable of detecting said specific type of microorganism;
   d. determining one or more fluorescence parameters for each of the two tubes;
   e. comparing for each of the tubes such one or more fluorescence parameters;
wherein the presence of said specific type of microorganism in the biological sample having the phenotype of resistance to said predetermined therapeutic agent is detected if the one or more fluorescence parameters of both tubes is substantially similar.

2. A method for detecting, in an uncultured biological sample comprising microorganisms, the presence of a specific type of microorganism resistant to a predetermined therapeutic agent, comprising the following steps:
   a. making two microbial suspensions of the sample in culture media, one in a first tube with, and one in a second tube without, such predetermined therapeutic agent
   b. incubating both such suspensions;
   c. adding to the tube containing each such suspension a fluorescent marker which is capable of detecting said specific type of microorganism;
   d. determining one or more flow cytometric parameters by performing flow cytometry on each of the two tubes;
   e. comparing for each of the tubes such one or more flow cytometric parameters;
wherein the presence of said specific type of microorganism in the biological sample having the phenotype of resistance to said predetermined therapeutic agent is detected if the one or more flow cytometric parameters of both tubes is substantially similar.

3. The method according to claim 2 wherein the one or more flow cytometric parameters comprise forward scatter and/or side scatter and/or fluorescence scatter parameters.

4. The method according to claim 3 wherein the parameters of the fluorescence scatter signal comprise intensity, spectral profile and/or cell count.

5. The method according to claim 2 further comprising one or more preparatory steps:
   i. identifying the type of microorganism present in the biological sample and according to such identification selecting the therapeutic agent or agents;
   ii. concentrating the biological sample and removing, if present, any detritus.

6. The method according to claim 1 wherein the uncultured biological sample is a direct sample of urine, a blood culture, or water.

7. The method according to claim 1 further comprising a centrifugation step or filtration step.

8. The method according to claim 1 wherein step a) further comprises including at least one lysing agent in microbial suspension.

9. The method according to claim 1 wherein the incubation time in the step b. is between 30 minutes and 2 hours.

10. The method according to claim 1 wherein the incubation temperature is between 25 and 35° C.

11. The method according to claim 1 wherein in step c. the fluorescent marker is present for a reaction time between 5 and 60 minutes.

12. The method according to claim 1 wherein the biological sample in step d. further comprises an enzymatic inhibitor if the presence of extended spectrum beta-lactamases (ESBLs) is detected.

13. The method according to claim 1 which further comprises the following steps:
   i. making two microbial suspensions of the sample in culture media
   ii. inoculating both suspensions with a carbapenem;
   iii. incubating the samples;
   iv. removing the microorganism from the first tube;
   v. adding to the first tube a control strain with a known carbapenem dose-effect curve;
   vi. adding to both samples a fluorescent marker capable of detecting both the control strain and the microorganism being tested;
   vii. determining one or more flow cytometric parameters by performing flow cytometry on each of the two tubes;

viii. Identifying the microorganism being tested as a carbapenemase producer if the effect of carbapenem on the control strain is less than what would be expected based on its known carbapenem dose-effect curve.

14. The method according to claim 1 wherein the said microorganism is a bacteria, a fungi or a protist, wherein the bacteria is a gram positive or negative; gram variable or bacteria unable to Gram stain; or an alcohol-acid resistant bacteria.

15. The method according to claim 1 wherein the microorganism is a *Staphylococcus* spp, *Streptococcus* spp, *Enterococcus* spp; Enterobacteriacea, *Escherichia coli, Klebsiella pneumonia, Proteus* spp; *Pseudomonas aeruginosa, Acinetobacter baummanii, Burkloderia cepaciae; Neisseria* spp, *Haemophilus* spp; *Mycobacteria* spp, *Nocardia* spp; *Legionella* spp, an anaerobic bacteria; *Candida* spp, *Cryptococcus neoformans, Pneumocystis jirovecii*, or a mould.

16. The method according to claim 1 wherein the therapeutic agent is an antibacterial drug selected from the group consisting of penicillins, cephalosporins, carbepenems, aztreonam, macrolides, quinolones, aminoglycosides, glycopeptides, a lipopeptide, tetracyclines colistin, chloramphenicol, clindamycin, fosfomycin, linezolid, nitrofurantoin, sulphonamide, rifampin, trimethoprim, trimethoprim-sulfamethoxazole or tigecycline, polyenes, 5-fluorocytosine, azoles or echinocandins.

17. The method according to claim 1 wherein the fluorescent marker is a nucleic acid stain, a metabolic stain, a membrane potential stain, a probe for organelles, a fluorescent tracer of cell morphology and fluid flow, a probe for cell viability, proliferation and function or a probe for reactive oxygen species.

18. The method according to claim 17 wherein the fluorescent marker is an acridine dye, cyanine dye, fluorone dye, oxazin dye, phenanthridine dye, or a rhodamine dye.

19. The method according to claim 1 wherein the uncultured biological sample is a suspension of microorganisms.

\* \* \* \* \*